US011548785B2

(12) United States Patent
Klok et al.

(10) Patent No.: US 11,548,785 B2
(45) Date of Patent: Jan. 10, 2023

(54) PROCESS TO CONVERT BISULPHIDE TO ELEMENTAL SULPHUR

(71) Applicant: Paqell B.V., Utrecht (NL)

(72) Inventors: Johannes Bernardus Maria Klok, Rhenen (NL); Annemiek Ter Heijne, Rhenen (NL); Frederikus De Rink, Amersfoort (NL); Cees Jan Nico Buisman, Harich (NL)

(73) Assignee: PAQELL B.V., Utrecht (NL)

( * ) Notice: Subject to any disclaimer, the term of this patent is extended or adjusted under 35 U.S.C. 154(b) by 419 days.

(21) Appl. No.: 16/616,641

(22) PCT Filed: May 30, 2018

(86) PCT No.: PCT/EP2018/064151
§ 371 (c)(1),
(2) Date: Nov. 25, 2019

(87) PCT Pub. No.: WO2018/219991
PCT Pub. Date: Dec. 6, 2018

(65) Prior Publication Data
US 2020/0109052 A1  Apr. 9, 2020

(30) Foreign Application Priority Data
Jun. 1, 2017 (EP) ..................... 17173888

(51) Int. Cl.
| | |
|---|---|
| *C01B 17/05* | (2006.01) |
| *B01D 53/84* | (2006.01) |
| *C02F 3/00* | (2006.01) |
| *C02F 3/28* | (2006.01) |
| *C02F 3/34* | (2006.01) |
| *G01N 27/49* | (2006.01) |
| *C12P 3/00* | (2006.01) |
| *C12Q 3/00* | (2006.01) |

(52) U.S. Cl.
CPC .............. *C01B 17/05* (2013.01); *B01D 53/84* (2013.01); *C02F 3/006* (2013.01); *C02F 3/28* (2013.01); *C02F 3/345* (2013.01); *C12P 3/00* (2013.01); *C12Q 3/00* (2013.01); *G01N 27/49* (2013.01); *C02F 2209/36* (2013.01); *C02F 2305/06* (2013.01)

(58) Field of Classification Search
None
See application file for complete search history.

(56) References Cited

U.S. PATENT DOCUMENTS 6,045,695 A * 4/2000 Janssen ............... C02F 3/345
                                                          210/916
2011/0011799 A1  1/2011 Rozendal et al.

FOREIGN PATENT DOCUMENTS

| CN | 105176614 A | 12/2015 |
|---|---|---|
| EP | 0958251 B1 | 10/2002 |
| EP | 3034157 A1 | 6/2016 |
| WO | 2009/101090 A1 | 8/2009 |
| WO | 2012011984 A1 | 1/2012 |
| WO | 2015/144069 A1 | 8/2015 |

OTHER PUBLICATIONS

Auguet et al. "Implications of downstream nitrate dosage in anaerobic sewers to control sulfide and methane emissions." Water Research 68: 522-532 (2015).
Blázquez et al. "Treatment of high-strength sulfate wastewater using an autotrophic biocathode in view of elemental sulfur recovery." Water Research 105: 395-405 (2016).
Norris et al. "Characteristics of *Sulfobacillus acidophilus* sp. nov. and other moderately thermophilic mineral-sulphide-oxidizing bacteria." Microbiology 142(4): 775-733 (1996).
DataBase WPI, Week 200834, Thomson Scientific, London, GB; AN 2008-E93704; Apr. 24, 2008 abstract.
Database WPI Week 201631 Thomson Scientific, London, GB; AN 2016-00314G XP002773390, & CN 105176614 A (Chengdu Biology Res Inst Chinese Acad O) Dec. 23, 2015 (Dec. 23, 2015) abstract.

* cited by examiner

*Primary Examiner* — David W Berke-Schlessel
(74) *Attorney, Agent, or Firm* — Nixon Peabody LLP; Ronald I. Eisenstein; Nicole D. Kling

(57) ABSTRACT

The invention is directed to a control method for a process to convert bisulphide to elemental sulphur in an aqueous solution comprising sulphide-oxidising bacteria wherein the process is controlled by applying a potential between the anode electrode and the cathode electrode or between the anode electrode and the reference electrode of an electrochemical cell resulting in a current between the cathode electrode and the anode electrode, measuring a current as measured by an electrochemical cell and adapting the process in response to the measured current. The process to convert bisulphide may comprise the following steps: (a) contacting bisulphide with oxidised sulphide-oxidising bacteria in the aqueous solution and elemental sulphur, (b) oxidizing the reduced sulphide-oxidising bacteria, (c) using the oxidised sulphide-oxidising bacteria obtained in step (b) in step (a) and (d) isolating elemental sulphur from the aqueous solution obtained in step (a) and/or step (b).

16 Claims, 3 Drawing Sheets

PROCESS TO CONVERT BISULPHIDE TO ELEMENTAL SULPHUR

CROSS-REFERENCE TO RELATED APPLICATIONS

This application is a 35 U.S.C. § 371 National Phase Entry Application of International Application No. PCT/EP2018/064151 filed May 30, 2018, which designates the U.S. and claims benefit under 35 U.S.C. § 119(a) of EP Provisional Application 17173888.3 filed Jun. 1, 2017, the contents of which are incorporated herein by reference in their entireties.

The invention is directed to a control method for a process to convert bisulphide to elemental sulphur in an aqueous solution comprising sulphide-oxidising bacteria.

EP0958251B describes a process for the biological treatment of an aqueous caustic solution containing sulphides. The sulphides are partly converted to elemental sulphur and partly to sulphate in the presence of sulphide-oxidising bacteria. According to this publication the microbiological oxidation of sulphide to elemental sulphur occurs either under oxygen limited circumstances, that is at DO (Dissolved Oxygen) values below, at least, 0.1 mg·L$^{-1}$ or under high sulphide loading rates. In the latter case, the biomass is overloaded and sulphur is formed as intermediate product. At loading rates below 250 mg sulphide L$^{-1}$ h$^{-1}$, the sulphide-oxidising bacteria tend to produce undesired sulphate rather than sulphur at increasing DO-values because sulphate formation yields more energy for microbial growth. Processes are preferably not operated under 'overload conditions' for the sake of process-stability. Therefore, a stoichiometrical oxygen supply is required to oxidise all sulphide into elemental sulphur. Since the detection limit of currently available oxygen sensors is about 0.1 mg·L$^{-1}$, they are not suitable as a measuring device and therefore another parameter is described in EP0958251B. The described method to control the oxygen supply is by measuring the redox (reduction-oxidation) potential of the solution. The redox potential is a measure of the solution's tendency to accept or donate electrons. The publication describes that in a sulphide oxidising bioreactor, the measured redox potential will predominantly be determined by the sulphide concentration. The process is controlled by adding more oxygen when the redox potential indicates a higher content of sulphide and vice versa.

The control method using the Redox Potential as described in EP0958251 has proven to be a very useful tool to control the process, for example on an hourly scale. A disadvantage of this method is that it does not provide any information regarding the biological activity of the sulphide-oxidising bacteria itself. It is possible that a process is seemingly correctly controlled within the redox set points while the biological activity of the sulphide-oxidising bacteria gradually drops over days to a level wherein H$_2$S removal efficiency is reduced, excessive consumption of chemicals takes place or even shut down of the process. The currently used method to measure the biological activity of the sulphide-oxidising bacteria is the so-called respiration test. In such a test a sample of aqueous solution is taken from the aerobic reactor or its effluent and saturated with oxygen. Next a known quantity of bisulphide is added and the decrease of dissolved oxygen is measured in time. Such an experiment is suitably performed in triplicate. The rate of decrease in dissolved oxygen is a measure of the ability of the sulphide-oxidising bacteria to convert bisulphide to elemental sulphur and sulfate. This measure is used to adapt the process conditions in especially the aerobic reactor.

Such a respiration test is time consuming and not suited for a simple on-line measurement and process control. For example the results may only be obtained after one or more days which is not optimal for controlling a process. Moreover, this test is not representative for a process as described in WO2015/114069. This publication describes a process wherein bisulphide and the sulphide-oxidising bacteria are contacted under anaerobic conditions in a first bioreactor. At these anaerobic conditions the sulphide-oxidising bacteria are capable of converting bisulphide to elemental sulphur. In a subsequent aerobic step the sulphide-oxidising bacteria are regenerated. The regenerated sulphide-oxidising bacteria are recycled to the anaerobic first bioreactor. In such a process the sulphide-oxidising bacteria convert bisulphide to elemental sulphur in the absence of oxygen. Because the respiration test is performed by saturating the aqueous solution with oxygen it follows that no representative measurement for the ability of the sulphide-oxidising bacteria to convert bisulphide for this process can be obtained with this test.

It is an object of the present invention to provide a simple control method for a process to convert bisulphide to elemental sulphur in an aqueous solution comprising sulphide-oxidising bacteria.

This is achieved by the following control method. A control method for a process to convert bisulphide to elemental sulphur in an aqueous solution comprising sulphide-oxidising bacteria wherein the control method comprises providing an electrochemical cell comprising a cathode electrode, an anode electrode and a reference electrode, wherein the electrodes are in contact with the aqueous solution, wherein a potential is applied, the applied potential, between the anode electrode and the cathode electrode or between the anode electrode and the reference electrode resulting in a current between the cathode electrode and the anode electrode, wherein the current is measured running between the cathode electrode and the anode electrode while maintaining a constant potential between the anode electrode and the cathode electrode or while maintaining a constant potential between the anode electrode and the reference electrode and adapting the process in response to the measured current.

Applicant found that the current as measured in an electrochemical cell at a set applied potential is a reliable measure of the ability of the sulphide-oxidising bacteria to convert bisulphide to elemental sulphur and/or the ability of the sulphide-oxidising bacteria to convert bisulphide to the undesired sulphate for both the earlier described aerobic processes and anaerobic processes. The measurement can be performed on-line or off-line. Currents can be measured in real time and provide real time information on the ability of the sulphide-oxidising bacteria to convert bisulphide to elemental sulphur. This results in more direct and effective process control as compared to control methods using the prior art respiration test and/or the redox potential.

Applicants have found that sulphide oxidizing bacteria are able to oxidize bisulphide to elemental sulfur in the absence of oxygen. The oxidation of sulphide can be described by:

$$HS^- + bac^+ \rightarrow \tfrac{1}{8}S_8 + H^+ + bac^- \qquad (1)$$

Here, bac$^+$ is an oxidized sulphide-oxidising bacteria. While bisulphide is oxidized, the bacteria is reduced (bac$^-$). To regenerate the bacteria they are contacted with for example oxygen as supplied to for example a regenerator reactor. The reduction of oxygen is given by:

 (2)

We have now found that the reduced sulphide-oxidising bacteria (bac−) are able to transfer electrons to an anode in an electrochemical cell. This finding enables one to use such a cell and measure the current when applying potential, which is a measure of the bioactivity, i.e. the ability of the sulphide-oxidising bacteria to convert bisulphide to elemental sulphur.

The current as measured by the electrochemical cell in the process according to the invention may for example be used to (i) provide information regarding the rate at which bacteria are regenerated and wherein the regeneration process may be adapted in response the measured current by for example adding more or less oxidant, for example oxygen, (ii) provide information regarding the total activity of bacteria and/or biomass concentration and wherein the process may be adapted by adding more or less nutrients, (iii) provide information regarding the concentration of dissolved bisulphide in a loaded aqueous solution and wherein the process may be adapted by adding more or less oxidised sulphide-oxidising bacteria to said loaded aqueous solution, and/or (iv) provide information regarding the potential of the bacteria to form the undesired by-product sulfate, wherein the process may be adapted by reducing the supply of electron acceptor to the process, for example oxygen and nitrate.

The electrochemical cell comprises a cathode electrode, an anode electrode and a reference electrode. More electrodes may be present, for example to measure currents simultaneously under different conditions. The electrodes are in contact with the aqueous solution. The current is measured running between the cathode and the anode electrode while maintaining a constant potential, between the anode and the cathode electrode or between the anode and the reference electrode. The measured current at an applied potential will provide a measure for the rate of electron transport from bacteria to anode and will thus reflect the activity of the bacteria. The measured current will provide a measure for the extent to which the bacteria have taken up sulphide and to what extent charge has been stored by the sulphide-oxidising bacteria. If the current decreases a decrease in activity of the sulphide-oxidising bacteria is measured and vice versa.

The applied potential is suitably between −1.0 V and 1 V and preferably between −0.6 V and 0.4 V expressed as the anode potential versus a Ag/AgCl reference. The current as measured is thereby not zero, suitably higher than 1 microA and preferably greater than 0.001 A/m² anode electrode area.

Preferably, the current is measured running between the cathode and the anode electrode while varying the applied potential between the anode and cathode electrode or between anode and the reference electrode. Thus, the current is measured at more than one different values for the applied potential. Preferably the current as measured for at least one value of the applied potential is greater than 0.001 A/m² anode electrode area. Such a measurement, which may be performed as a linear sweep voltammetry, cyclic voltammetry, or as polarization curve, is advantageous because it provides a quick measurement of biological activity in terms of electrode potential and current. This provides the operator or the process control algorithm input regarding the extent to which the bacteria have taken up sulphide which can be used to regulate oxygen supply when regenerating the sulphide-oxidising bacteria.

The electrochemical cell may be controlled by a potentiostat, a resistance and/or and external power source in a manner known to the skilled person.

The cathode electrode may be made of any conductive material like for example carbon-based electrodes or titanium-based electrodes, with or without catalyst coatings to increase the reaction rate. A preferred metal for the cathode is platinum for its good performance as hydrogen producing catalyst. The anode may be made of any conductive material, like carbon, graphite, titanium with coating. Preferred materials for the anode is graphite. The reference electrode can be any type, for example a Ag/AgCl electrode and more suitably a saturated calomel electrode (SCE).

The measurement is preferably performed in the absence of dissolved oxygen and preferably at anaerobic conditions, such to minimize the influence of other electron acceptors next to the electron acceptors on the electrode on the measured potential. The measurements may be performed on-line or off-line.

The process to convert bisulphide to elemental sulphur in an aqueous solution comprising sulphide-oxidising bacteria preferably comprises at least the following steps:

(a) contacting bisulphide with oxidised sulphide-oxidising bacteria in the aqueous solution to obtain reduced sulphide-oxidising bacteria and elemental sulphur, (b) oxidizing the reduced sulphide-oxidising bacteria to obtain oxidised sulphide-oxidising bacteria, (c) using the oxidised sulphide-oxidising bacteria obtained in step (b) in step (a) and (d) isolating elemental sulphur from the aqueous solution obtained in step (a) and/or step (b).

The process as described above may be a process such as described in for example the earlier referred to EP0958251B, WO2015/114069 or U.S. Pat. No. 5,976,868. The aqueous solution comprising bisulphide and oxidised sulphide-oxidising bacteria of step (a) may be obtained as described in these publications. The solution may be obtained by combining an aqueous solution of oxidised sulphide-oxidising bacteria with a spent caustic solution comprising bisulphide or with an alkaline absorbing solution used for absorbing hydrogen sulphide or other reduced sulphur compounds from a sour gas stream. Alternatively, the aqueous solution may be obtained by dissolving hydrogen sulphide from a highly concentrated or essentially pure hydrogen sulphide gas into an aqueous solution comprising oxidised sulphide-oxidising bacteria by means of an injector.

Preferably step (a) is performed by contacting an aqueous solution comprising oxidised sulphide-oxidising bacteria with a gas comprising hydrogen sulphide. Such contacting is preferably performed in a gas absorber in which the aqueous solution comprising oxidised sulphide-oxidising bacteria is contacted with a gas comprising hydrogen sulphide to obtain a loaded aqueous solution. In such a gas absorber gas and aqueous solution contact each other counter-currently. It is found that by performing such contacting in the presence of oxidized sulphide-oxidising bacteria a more efficient absorption of hydrogen sulphide is achieved. Part of the conversion of bisulphide to elemental sulphur will take place in such a gas absorber. In order to achieve a higher conversion it is preferred that the loaded aqueous solution is provided to a bio-reactor. By combining the gas absorber with such a bioreactor the total residence time can be such that an acceptable conversion to elemental sulphur is achieved. A further advantage is that fresh oxidized sulphide-oxidising bacteria can be provided to such a bioreactor to further enhance this conversion to elemental sulphur. Step (a) involving the above gas absorber and the optional bioreactor are preferably performed under anaerobic conditions.

The bisulphide concentration in the aqueous solution in (a) is not critical. Solutions with bisulphide concentrations (expressed as sulphur) as high as 20 grams per litre or even higher may be used. In such a calculation also the sulphur which has been taken up by the sulphide-oxidising bacteria is included. Preferably, the bisulphide concentration in the aqueous solution is in the range of from 100 mg/L to 15 g/L, more preferably of from 150 mg/L to 10 g/L.

The contacting (a) of the aqueous solution comprising bisulphide with oxidised sulphide-oxidising bacteria is suitably performed under anaerobic conditions. With anaerobic conditions is meant in the absence of molecular oxygen. No molecular oxygen is supplied and/or present during such contacting. Preferably such contacting is performed in the absence of other oxidants such as nitrate. Anaerobic conditions is here meant 'in the absence of molecular oxygen' wherein the concentration of molecular oxygen in the aqueous solution is at most 1 μM, more preferably at most 0.1 μM.

The sulphide-oxidising bacteria may be any sulphide-oxidising bacteria, preferably the sulphide-oxidising bacteria is of one of the following strains: Halothiobacillus, Thioalkalimicrobium, Thioalkalispira, Thioalkalibacter, Thioalkalivibrio, Alkalilimnicola, Alkalispirillum and related bacteria. These haloalkaliphilic sulphide-oxidising bacteria are suited for this process. The bacteria may be used as such, i.e. may be present as planktonic cells the aqueous solution, or may be supported on a dispersed carrier.

The contacting (a) of the aqueous solution comprising bisulphide with oxidised sulphide-oxidising bacteria may take place at any suitable conditions of temperature, pressure and hydraulic residence time suited for performing the biological oxidation of bisulphide into elemental sulphur. Preferably the temperature is in the range of from 10 to 60° C., more preferably of from 20 to 40° C. The pressure is suitably in the range of from 0 bara to 100 bara, more preferably of from atmospheric pressure to 80 bara. The pH of the aqueous solution is suitably in the range of from 7 to 10, more preferably in the range of from 7.5 to 9.5. The salinity of the aqueous solution as expressed as molar concentration of cations, and preferably molar concentration of total cations of sodium and/or potassium, is preferably between 0.3 and 4 M and more preferably between 0.5 and 1.5 M. The aqueous solution may comprise trace compounds of several different compounds, such as for example iron, copper or zinc, as nutrients for the sulphide-oxidising bacteria.

The residence time in step (a) in case of a continuous process or contact time in case of a batch process is preferably at least 3 minutes, more preferably at least 5 minutes, more preferably at least 10 minutes. The maximum residence time is not critical, but for practical reasons, the residence time is preferably at most 2 hours, more preferably at most 1 hour. Preferably the weight ratio of nitrogen as part of the total of the sulphide-oxidising bacteria and total amount of bisulphide is at least 0.1 mg N/mg bisulphide, preferably at least 0.5 mg N/mg bisulphide, more preferably at least 0.7 mg N/mg bisulphide.

The contacting in the gas absorber in step (a) may be performed by well known processes for absorption of bisulphide. The gas temperature may be in the range of from 0° C. to 100° C., preferably of from 20° C. to 80° C., more preferably of from 25° C. to 50° C. and a pressure in the range of from 0 bara to 100 bara, preferably of from atmospheric pressure to 80 bara. The liquid alkaline absorbent may be any liquid alkaline absorbent known to be suitable for absorption of hydrogen sulphide, i.e. known to dissolve sulphides. Examples of suitable liquid alkaline absorbents are carbonate, bicarbonate and/or phosphate solutions, more preferably a buffered solution comprising carbonate and bicarbonate. Buffered solutions comprising sodium or potassium carbonate and bicarbonate are particularly preferred, more in particular a buffered solution comprising sodium carbonate and sodium bicarbonate. The pH of the liquid alkaline absorbent that is supplied to the upper part of the absorption column, is preferably in the range of from 7 to 10, more preferably of from 7.5 to 9.5.

Preferably such an absorption is performed in an absorption column wherein the hydrogen sulphide comprising gas stream is contacted in the absorption column with all or preferably part of a liquid effluent as obtained in step (b). Part of the liquid effluent as obtained in step (b) is directly recycled to the bioreactor of step (a). The liquid effluent of step (b) may before being recycled to the gas absorber and/or to the bioreactor of step (a) or be subjected to step (d). Part of the effluent poor in elemental sulphur as obtained in step (d) may be purged. Step (d) may be performed by well-known process steps such as in the sulphur separator described in U.S. Pat. No. 5,976,868.

The process of the present invention is especially suited to control step (b) of the above process. For an efficient process it is important that the ability of the sulphide-oxidising bacteria to convert bisulphide to elemental sulphur is above certain minimum values and more preferably around a constant value. This ability can now be measured quickly and accurately by measuring a current using an electrochemical cell. Therefore it is preferred that the current as measured by an electrochemical cell is measured by contacting the electrodes of the electrochemical cell with an aqueous solution comprising oxidised sulphide-oxidising bacteria as obtained in step (b). If the current is too low the rate of oxidation in step (b) may be increased to increase this ability. In this manner one can ensure that the capacity to absorb hydrogen sulphide in for example a gas absorber is sufficient and the hydrogen sulphide levels in the obtained gas is below the required levels.

The process may also be performed by contacting the electrochemical cell with the loaded aqueous solution as it is obtained in the above referred to gas absorber. Especially in a process wherein the loaded aqueous solution is provided to a bioreactor operated under anaerobic conditions. In this manner one can control the amount of oxidised sulphide-oxidising bacteria which is directly recycled from step (b) to this anaerobic operated bioreactor. The loaded aqueous solution may comprise dissolved bisulphide next to bisulphide which has already been absorbed by the bacteria itself. If the loaded aqueous solution contains a high level of dissolved bisulphide it may be advantageous to directly recycle more oxidised sulphide-oxidising bacteria to the bioreactor operated under anaerobic conditions. In this manner, the conversion of the dissolved bisulphide in the loaded aqueous solution may be enhanced in the bioreactor operated under anaerobic conditions. The content of dissolved bisulphide may be measured on the loaded aqueous solution with sensors based on analytical methods like a chemical sensors.

In addition to measuring a current the concentration of bacteria may also be measured. The concentration of bacteria may be measured as the amount of total N-organic as based on the absorbance of nitrophenol at 370 nm, with the Hach Lange cuvette test LCK138. By measuring the concentration of bacteria in combination with the current one may find that the process requires more or less nutrients. In response to the to the measured current and measured bacteria concentration the process is therefore suitably adapted by adapting the amount of nutrients added to the process.

Step (b) is suitably performed by contacting the reduced sulphide-oxidising bacteria with an oxidant. Such an oxidant may be oxygen or nitrate. In such a process it is preferred to measure the current by the electrochemical cell by contacting the electrodes of the cell with the aqueous solution obtained in step (b) and wherein the process is adapted in response of the measured current by adjusting the rate of oxidation in step (b).

The invention will be illustrated by FIG. 1 which shows a process which may be controlled by the process according to the invention. A hydrogen sulphide and carbon dioxide comprising gas is supplied via line 1 to a gas absorber 2. To said gas absorber 2 also an aqueous alkaline solution further comprising oxidized sulphide-oxidising bacteria is supplied via line 3. Via line 5 a loaded aqueous solution comprising bisulphide compounds, sulphide-oxidising bacteria and elemental sulphur is discharged from said gas absorber 2 and via line 4 a gas having a lower content of hydrogen sulphide is discharged from said gas absorber. In bioreactor 6 the loaded aqueous solution as supplied via line 5 is kept under anaerobic conditions for at least a time sufficient to lower the concentration of dissolved bisulphide to below 5 mM. To said first bioreactor 6 an aqueous alkaline solution further comprising oxidized sulphide-oxidising bacteria is supplied via line 13. In regenerator 8 the loaded aqueous solution as discharged from bioreactor 6 via line 7 is contacted with air as an oxidant as supplied via line 9 to oxidise the reduced sulphide-oxidising bacteria. Via line 11 a liquid effluent comprising oxidised sulphide-oxidising bacteria is discharged to the gas absorber 2 via line 12, directly to the bioreactor 6 via line 13 and to the separator 15. In separator 15 precipitated solid elemental sulphur is separated from the effluent to obtain a sulphur-depleted effluent which is recycled to the regenerator 8 via line 16 and solid elemental sulphur which is withdrawn from the process via line 17. Part of the sulphur-depleted effluent is purged from the process via line 18. Preferred aqueous compositions which can be measured using the 3 electrode cell according to the process of this invention are the aqueous solutions in lines 11, 12, 3, 13, 5 and 7. Most preferred in lines 11 or 12 and 5.

EXAMPLE 1

Figure 1:
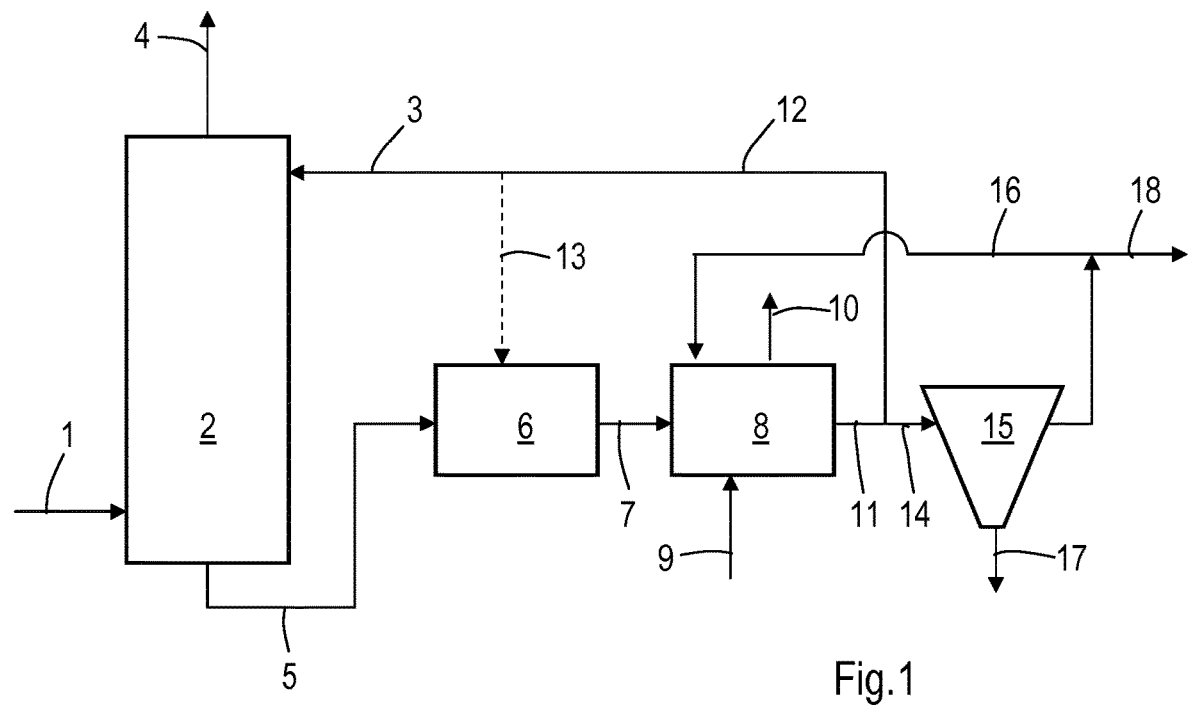
FIG. 1 shows a process which may be controlled by the process of this invention.
Figure 2:
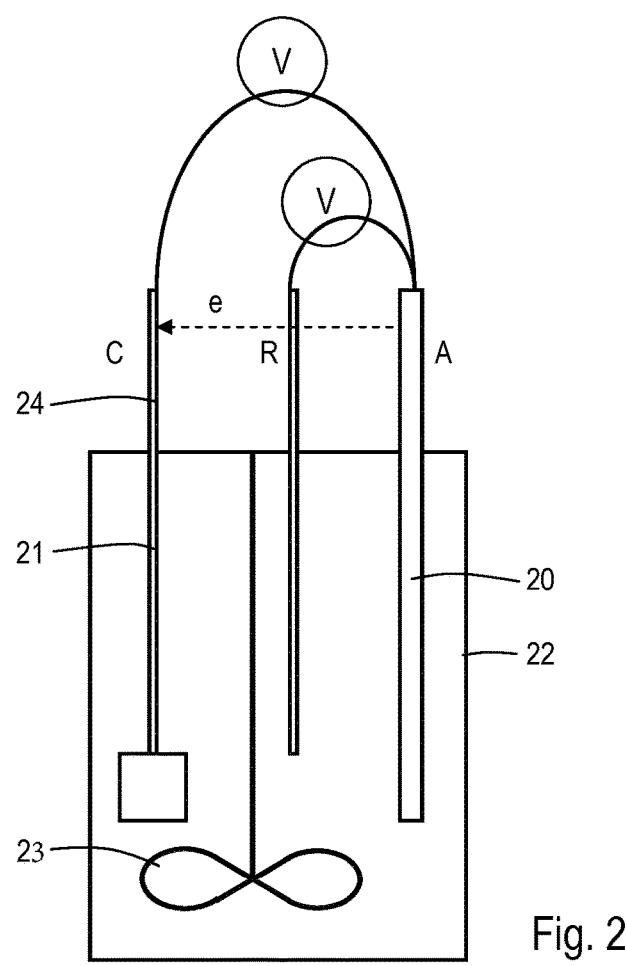
FIG. 2 shows an electrochemical cell
Figure 3:
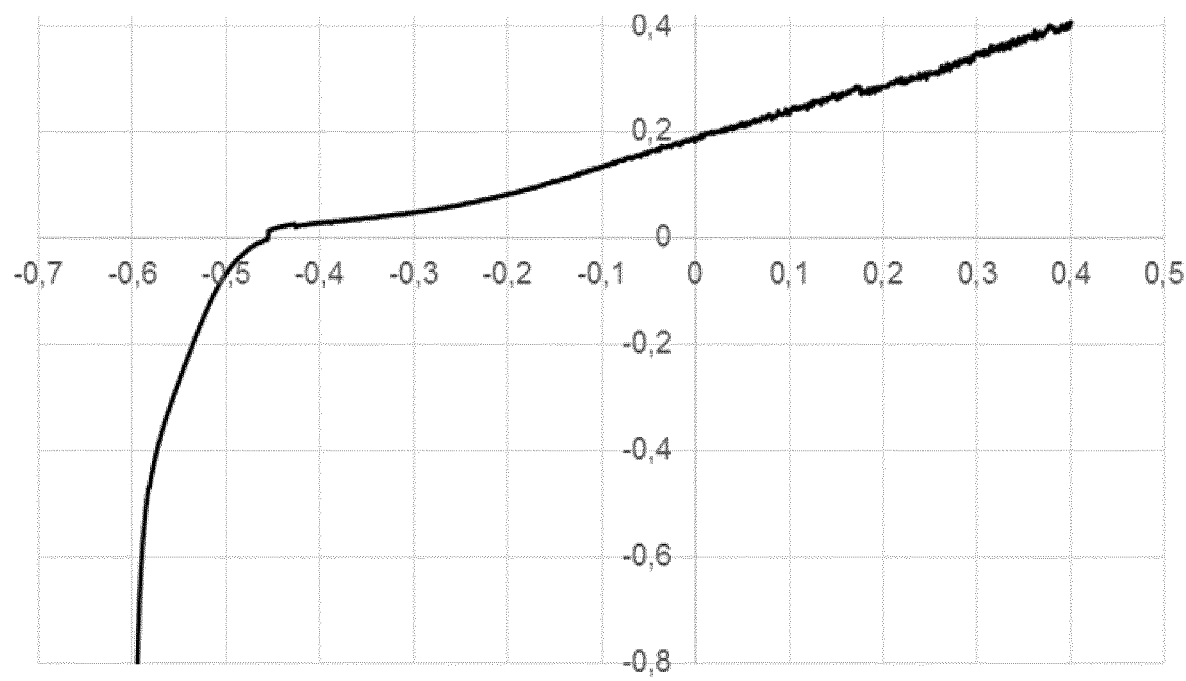
FIG. 3 shows the measured current on the y-axis and the potential between anode and reference electrode on the x-axis of Example 1.

In this example an electrochemical cell, controlled by a potentiostat, is used as illustrated in FIG. 2. The cell contains a graphite rod as the anode (A), a platinum foil as the cathode (C), and a Ag/AgCl electrode as the reference electrode (R). During a measurement, the current (electron flow) between anode and cathode is measured for a known anode potential (compared to the reference). For a typical aqueous solution as sampled in line 12 of FIG. 1 the current was measured using this 3-electrode cell at varying potentials between anode and reference electrode. The experiment was executed as a so-called linear sweep. The results are shown in FIG. 3, wherein the measured current is on the y-axis and the potential between anode and reference electrode is on the x-axis. In this measurement the initial anode potential is −0.6 V and is increased with 1 mV/s until 0.4V. If the measured current is negative (<0 mA) it means electrons flow from cathode to anode, in case it is positive (>0), electrons flow from anode to cathode, meaning that electrons are extracted from the bacteria. From below graph it can be deduced that with anode potentials of −0.45V and higher, reduced bacteria transfer their electrons to the anode. The higher the anode potential, the higher the driving force for electron transport between bacteria and electrode, and the higher the current. At a certain anode potential, a maximum current is reached as a result of maximum charge transfer rate or diffusion limitations. At potentials more negative than −0.45V, current is negative and electrons move from cathode to anode. In this situation, electrons are being transferred to the bacteria. The thus measured capacity to take in electrons of the bacteria is also an important process property suited to adapt the process.

EXAMPLE 2

Figure 4:
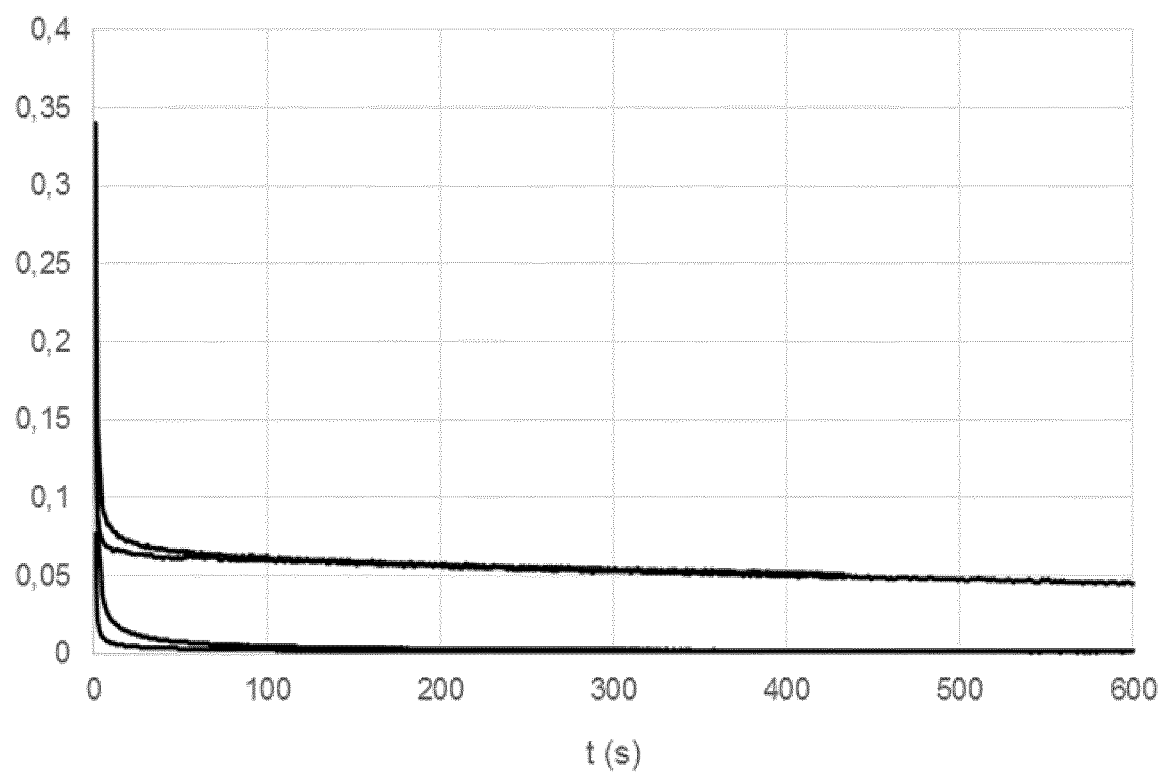
FIG. 4 shows the current measured against time of Example 2.

Using the same 3-electrode cell of Example 1 the current was measured in time of a sample of a typical loaded aqueous solution as sampled in line 11 of FIG. 1. The measurement was performed at a fixed anode potential of 0.1V. From a new sample, the bacteria were separated from the loaded aqueous solution and the same measurement was done. In FIG. 4 the results are shown wherein the upper two lines represent the current measured for the original loaded solution and the two lower lines is the current measured for the loaded solution without the bacteria. It shows that more charge can be extracted from solution with bacteria compared to solution without bacteria, showing that the bacteria have stored charge that they can release at an anode.

EXAMPLE 3

In this example a Sludge A containing haloalkaliphilic sulphide oxidising bacteria (HA-SOB) as obtained from a commercially operated biodesulfurization process which involved an absorber column and aerated bioreactor and a Sludge B containing haloalkaliphilic sulphide oxidising bacteria (HA-SOB) from a pilot scale process (pilot plant) which involved an absorber column, anaerobic and aerated bioreactor according to WO2015114069 was used. Samples of both sludges were taken from the aerated bioreactor. Both samples had a medium consisting of bicarbonate and carbonate at pH 8.5. The concentration biomass as total N was 72.4 mgN/L for Sludge A, and 29.2 mgN/L for Sludge B.

The experiment was performed in three steps. The biomass was actively aerated during a period of >12 hours. When oxygen levels remained saturated, oxygen was removed from solution by flushing with $N_2$. Then, the biomass was supplied with 0.2 mM sulphide (Analar NORMAPUR, VWR, analytical grade) as $Na_2S \cdot 3H_2O$. The solution was filtered using a 0.45 um filter and sulphide concentration was measured after 5 minutes.

Biomass was tested in an electrochemical cell for its ability to produce electric current. Total liquid volume of the single chamber cell was 50 mL (FIG. 2). The anode (20) was made of carbon and the external area in contact with liquid was 3 cm². The cathode (21) was made of Pt foil (2.82 cm2); a Pt wire made up the connection to the outside of the cell (22). A Ag/AgCl, 3 M KCl reference electrode was used (+0.205 V vs. SHE) and ionically connected to the solution via a capillary (24). All potentials are reported against this reference electrode. A magnetic stirrer (23) was used to ensure good mass transfer and the cell was operated at room temperature. Control experiments were performed with the solution without SOB by centrifuging the solution for 10 minutes at 10000 rpm and testing the supernatant in the electrochemical cell.

Anode potential was controlled versus the reference electrode with a potentiostat (Iviumstat, Eindhoven, The Netherlands) using chronoamperometry, the anode potential was controlled at +0.1 V versus the reference electrode. Linear sweeps were obtained at a scanrate of 1 mV/s in a range of anode potentials between −0.6 and +0.4 V In this example sulphide was added as $Na_2S \cdot 3H_2O$ (Analar NORMAPUR, VWR, analytical grade). 1 mL of anaerobic stock solution was added to 80 mL 4% (w/v) NaOH, with 1 mL of 30% (w/v) $NH_4OH$ to stabilize all present dissolved sulphide.

Anode coulombic efficiency was calculated as the total charge recovered divided by the total charge added in the form of sulphide. To assess the removal capacity of dissolved sulphide by HA-SOB, and their electron shuttle capacity in absence of external electron acceptors (oxygen), the sludge was submitted to the above described three-step preparation procedure. After addition of 0.2 mM sulphide the concentration of sulphide decreased from 0.2 mM initially to 0.056 mM after 5 minutes for sludge A, whereas for Sludge B, sulphide concentrations decreased to values below detection limit. Without SOB, also a slight decrease in sulphide concentration from 1.2 mM to 0.9 mM was observed, meaning that without microbial activity, also some sulphide was converted. Expressed per amount of biomass, the sulphide uptake was 5.2 mM S/g N for Sludge B and 0.6 mM S/g N for Sludge A.

Figure 5:
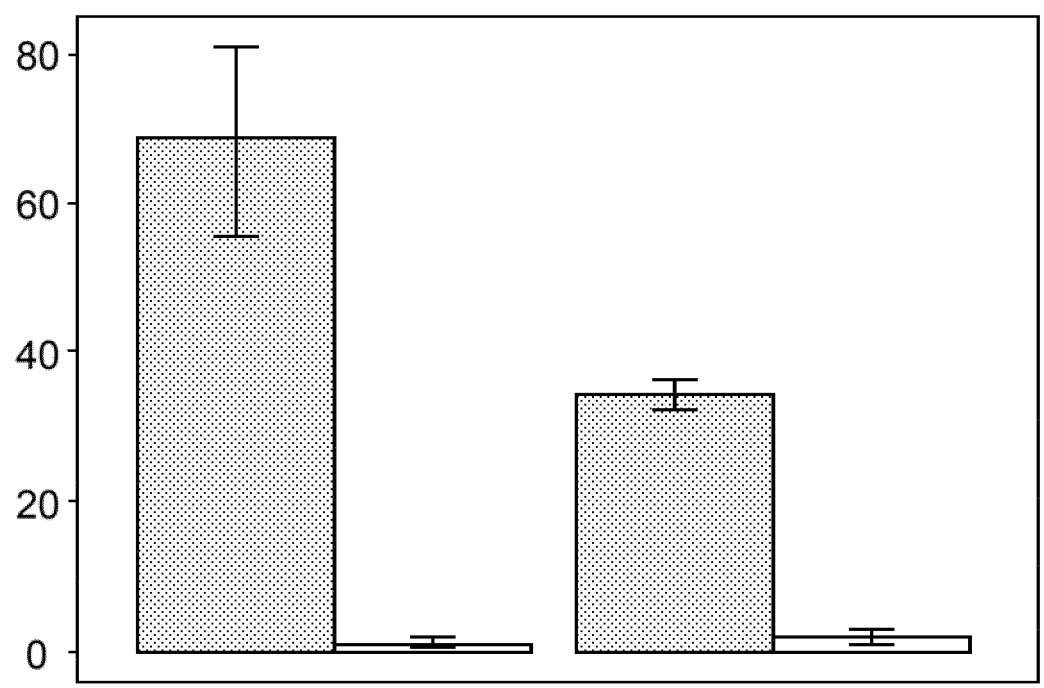
FIG. 5 shows the measured charge in mC for sludge A and sludge B of Example 3.

HA-SOB were tested for their ability to use the electrode as electron acceptor for sulphide oxidation or release of stored electrons. Current was measured in the electrochemical cell at +0.1 V vs Ag/AgCl anode potential. FIG. 5 shows the measured charge in mC for sludge B (left two bars) and sludge A (right hand bars). The smaller white bars represent measurement of only the medium of sludge B and A respectively. Charge was recovered from Sludge B (number of measurements: n=4) and Sludge A (number of measurements: n=2) in absence of sulphide and oxygen, including standard error. Total charge was higher for sludge B, even though biomass concentration was lower than for sludge A. Charge recovery over the first 600 seconds was minimal for medium without bacteria, showing that HA-SOB played the main role in electron transfer. Average current density was 481 mA/m² in the first 600 s for Sludge B and 239 mA/m². For sludge A.

Current was measured as function of anode potential at 0 V and +0.1 V vs Ag/AgCl Table 1 shows a measured charge, normalized to the amount of biomass (mC/mg N) for both sludges. Most charge was recovered at +0.1 V and the total charge decreased with decreasing anode potential. Sludge B again showed higher current densities than Sludge A.

TABLE 1

| Anode potential (vs Ag/AgCl) | Pilot (Sludge B) | Full-scale (Sludge A) |
|---|---|---|
| 0.1 V | 46.8 mC/mg N | 9.4 mC/mg N |
| 0 V | 26.3 mC/mg N | 6.4 mC/mg N |

EXAMPLE 4

Figure 6:
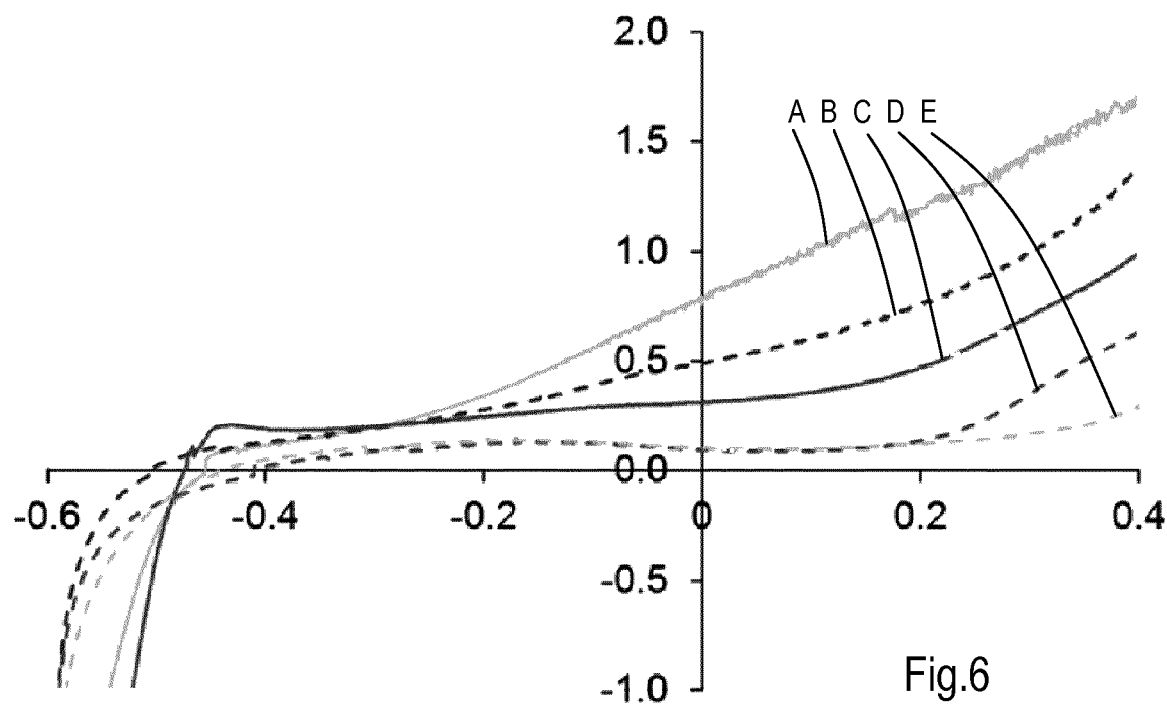
FIG. 6 shows the measured current against an applied anode potential range of Example 4.

A linear sweep was performed for both types of HA-SOB (sludge A and sludge B) and for both their mediums as described in Example 3 for an anode potential range between −0.6 and +0.4 V vs Ag/AgCl. At anode potentials >−0.45 V for sludge B, and at anode potentials >−0.48 for sludge A, the current changed from negative to positive values. At positive currents, electricity is recovered from the HA-SOB. Current increased with increasing anode potential and sludge B produced higher current than sludge A at more positive anode potentials. At more negative anode potentials between −0.48 and −0.3 V vs Ag/AgCl, sludge B produced higher current than sludge A. In absence of HA-SOB, current was considerably lower than with HA-SOB. FIG. 6 shows the results wherein line A is sludge B, line B is medium of Sludge B to which 0.2 mM sulphide is added, line C is sludge A, line D is medium of sludge A and line E is medium of Sludge B.

Results of measurement as described in example 3 and 4 can be used for control in a (full scale) biodesulfurization process. Biological activity, i.e. measurement of current production as described in example 3, can for example be used to determine the amount of sulphide the system can handle. Based on this, the total sulphide loading (directly proportional to the gas flow and $H_2S$ concentration in the sour gas) to the system can be adjusted. When found that bacterial activity is limited, nutrient dosing containing trace elements vital for bacterial growth can be increased to stimulate bacterial growth.

Furthermore, measurement of activity at different anode potentials (example 4) reveals how selective the system is towards sulfur and sulfate formation. This information can be used to optimize the amount of air supplied, for example by adjusting the ORP setpoint (Redox Potential set point), which is used to supply oxygen to the bioreactor. When the activity tests indicate an increased potential for sulfate formation, ORP setpoint can be lowered.

The invention claimed is:
1. A control method for a process to convert bisulphide to elemental sulphur in an aqueous solution comprising sulphide-oxidising bacteria wherein the control method comprises
   providing an electrochemical cell comprising a cathode electrode, an anode electrode and a reference electrode,
   wherein the electrodes are in contact with the aqueous solution,
   wherein a potential is applied, the applied potential, between the anode electrode and the cathode electrode or between the anode electrode and the reference electrode resulting in a current between the cathode electrode and the anode electrode and wherein reduced sulphide-oxidising bacteria transfer electrons to the anode electrode,
   wherein the current is measured running between the cathode electrode and the anode electrode at anaerobic conditions while maintaining a constant potential between the anode electrode and the cathode electrode or while maintaining a constant potential between the anode electrode and the reference electrode, wherein the measured current is a measure of the bioactivity of the sulphide-oxidising bacteria to convert bisulphide to elemental Sulphur, and adapting the process in response to the measured current.

2. The control method according to claim 1, wherein the applied potential is between −0.6 V and 0.4 V expressed as the anode potential versus a Ag/AgCl reference.

3. The control method according to claim 1, wherein the current is measured while varying the applied potential between the anode and cathode electrode.

4. The control method according to claim 3, wherein the current as measured for at least one value of the varying applied potential is greater than 0.01 A/m$^2$.

5. The control method according to claim 1, wherein the electrochemical cell is controlled by a potentiostat, a resistance and/or and external power source.

6. The control method according to claim 1, wherein the process to convert bisulphide to elemental sulphur comprises at least the following steps:
   (a) contacting bisulphide with oxidised sulphide-oxidising bacteria in the aqueous solution to obtain reduced sulphide-oxidising bacteria and elemental sulphur,
   (b) oxidizing the reduced sulphide-oxidising bacteria to obtain oxidised sulphide-oxidising bacteria,
   (c) using the oxidised sulphide-oxidising bacteria obtained in step (b) in step (a) and
   (d) isolating elemental sulphur from the aqueous solution obtained in step (a) and/or step (b).

7. The control method according to claim 6, wherein in step (a) an aqueous solution comprising oxidised sulphide-oxidising bacteria is contacted with a gas comprising hydrogen sulphide.

8. The control method according to claim 7, wherein step (a) is performed in a gas absorber in which the aqueous solution comprising oxidised sulphide-oxidising bacteria is contacted with a gas comprising hydrogen sulphide to obtain a loaded aqueous solution and in a bio-reactor to which the loaded aqueous solution is provided.

9. The control method according to claim 6, wherein step (a) is performed under anaerobic conditions.

10. The control method according to claim 6, wherein the current as measured by the electrochemical cell is measured by contacting the electrodes of the electrochemical cell with an aqueous solution comprising oxidised sulphide-oxidising bacteria as obtained in step (b).

11. The control method according to claim 8, wherein the current as measured by an electrochemical cell is measured by contacting the electrodes of the electrochemical cell with the loaded aqueous solution.

12. The control method according to claim 11, wherein in addition a current is measured by an electrochemical cell by contacting the electrodes of the electrochemical cell with the loaded aqueous solution from which the sulphide-oxidising bacteria have been removed and wherein this current is subtracted from the current measured for the loaded aqueous solution and wherein the resulting current is used as a measure for the ability of the sulphide-oxidising bacteria to convert bisulphide into elemental sulphur.

13. The control method according to claim 1, wherein in addition to measuring a current the concentration of bacteria is also measured and wherein in response to the to the measured current and measured bacteria concentration the process is adapted by adapting the amount of nutrients added to the process.

14. The control method according to claim 6, wherein step (b) is performed by contacting the reduced sulphide-oxidising bacteria with an oxidant.

15. The control method according to claim 14, wherein the oxidant is oxygen or nitrate.

16. The control method according to claim 6, wherein the current as measured by the electrochemical cell is measured by contacting the electrodes of the electrochemical cell with the aqueous solution obtained in step (b) and wherein the process is adapted in response of the measured current by adjusting the rate of oxidation in step (b).

* * * * *